United States Patent [19]

Wilke et al.

[11] 4,076,757

[45] Feb. 28, 1978

[54] 3-METHOXYCYCLOOCTADIENE-(1,5)

[75] Inventors: Günther Wilke; Paul Heimbach, both of Mulheim (Ruhr), Germany

[73] Assignee: Studiengesellschaft Kohle m.b.H., Mulheim (Ruhr), Germany

[21] Appl. No.: 737,766

[22] Filed: Nov. 1, 1976

Related U.S. Application Data

[60] Division of Ser. No. 585,287, Jun. 9, 1975, Pat. No. 4,032,585, which is a division of Ser. No. 463,087, Apr. 22, 1974, Pat. No. 3,929,921, which is a division of Ser. No. 109,949, Jan. 26, 1971, Pat. No. 3,849,506, which is a division of Ser. No. 843,220, Jul. 18, 1969, Pat. No. 3,586,727, and Ser. No. 845,901, Jul. 29, 1969, Pat. No. 3,629,347, and Ser. No. 845,904, Jul. 29, 1969, abandoned, each is a continuation-in-part of Ser. No. 582,775, Sep. 27, 1966, abandoned.

[30] Foreign Application Priority Data

Sep. 29, 1965 Germany .............................. 1493221

[51] Int. Cl.² ............................................. C07C 43/18
[52] U.S. Cl. ................................................ 260/611 R
[58] Field of Search ........................... 260/611 R, 611

[56] References Cited

U.S. PATENT DOCUMENTS 3,586,727  6/1971  Wilke et al. ..................... 260/611 R

OTHER PUBLICATIONS

S. Kohle, Chem. Abs., vol. 67, (1967), 73242y.

*Primary Examiner*—Bernard Helfin
*Attorney, Agent, or Firm*—Burgess, Dinklage & Sprung

[57] ABSTRACT

A series of mono, bi and tricarbocyclic compounds, most of which have olefinic unsaturation in the ring, which may or may not have substituents thereon. While the bi and tricyclic rings may be unsubstituted, these compounds which have olefinic unsaturation, particularly multiple olefinic unsaturation, are polymerizable and copolymerizable in known polymerization systems. They are particularly good crosslinking agents. These compounds are further useful in the sense that they can be cleaved oxidatively, to corresponding carboxylic acids, aldehydes and/or alcohols which have known utility in the plasticizer and detergent arts. The compounds which do not have olefinic unsaturation can also be oxidatively cleaved to produce oxygenated, e.g., acid, alcohol or aldehyde, compounds having known utility.

1 Claim, No Drawings

3-METHOXYCYCLOOCTADIENE-(1,5)

This is a division of application Ser. No. 585,287, filed June 9, 1975, now U.S. Pat. No. 4,032,585, which in turn is a division of application Ser. No. 463,087, filed Apr. 22, 1974, now U.S. Pat. No. 3,929,921, which in turn is a division of application Ser. No. 109,949, filed Jan. 26, 1971, now U.S. Pat. No. 3,849,506, which in turn is a division of each of applications Ser. Nos. 843,220, filed July 18, 1969, now U.S. Pat. No. 3,586,727; Ser. No. 845,901, filed July 29, 1969, now U.S. Pat. No. 3,629,347; and Ser. No. 845,904, filed July 29, 1969, now abandoned, each of which is in turn a continuation-in-part of Ser. No. 582,775, filed Sept. 27, 1966, now abandoned.

In these parent applications, a process has been described for the catalytic dimerization and trimerization, respectively, of 1,3-diolefins, in which catalysts are used which are produced by mixing carbonyl-free compounds of nickel with organometallic compounds such as metal alkyls, metal aryls, or Grignard compounds, or with metal hydrides or with metal hydride complex compounds and electron donors. The electron donors used are Lewis bases such as cyclic ethers, tertiary amines, especially cyclic tertiary amines, alkyl or aryl phosphines, especially triphenylphosphine, or alkyl or aryl phosphites or compounds with a carbon-to-carbon multiple bond. Similar processes are claimed in German Auslegeschrift No. 1,126,864 of Badische Anilin- und Sodafabrik, wherein the catalysts are made by the reduction of transitional metal compounds by means of metals (Al, Mg), and German Auslegeschrift No. 1,144,268, wherein certain nickel-(O) compounds are used as catalysts. Furthermore, it is known that butadiene can be transformed with the aid of catalysts, such as $(R_3P)_2Ni(CO)_2$, into mixtures of cyclooctadiene-(1,5) and 4-vinylcyclohexene by the methods described in German Pat. No. 881,511 and U.S. Pat. No. 2,686,209.

According to Austrian Pat. No. 232,495, the catalytic co-oligomerization of butadiene and ethylene, for example, results in the formation of cyclodecadiene-(1,5) compounds. According to all the processes described in the above-cited patents, substituted 1,3-diolefins can be used instead of butadiene-(1,3).

This invention is for the production of large mono, bi or tricyclic alicyclic rings of the formula:

$$A - \theta - B$$

wherein:

$\theta$ is a member selected from the group consisting of cyclooctadiene-(1,5), cyclododecatriene-(1,5,9), cyclodecadiene and cyclodecatriene;

A is a member selected from the group consisting of methyl, ethyl, vinyl, phenyl, buten-1-yl, buten-2-yl, methoxy and carboalkoxy having up to 10 carbon atoms and;

B is a member selected from the group consisting of hydrogen, methyl, ethyl, vinyl and a carboalkoxy of up to 10 carbon atoms wherein:

A and B can be linked together by a bridge of the formula:

[CH$_2$]$_{10}$ 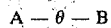 or by the groups

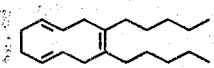 and  and

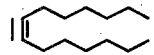

wherein:

When A is methyl and $\theta$ is a cyclooctadiene, said methyl is attached to a saturated carbon atom in said cyclooctadiene ring and provide further that where B is methyl, or a carboalkoxy group, A is methyl.

The products of this invention are made by the cyclooligomerization of at least two different conjugated dienes. There may also be present during the cyclooligomerization one or more other olefinically unsaturated monomers which cyclocooligomerize along with the conjugated dienes. Large, multicyclic rings are produced in this latter fashion.

The cyclo-cooligomerization of this invention can be performed with the aid of catalysts of zerovalent nickel such as those described in German Auslegeschrift No. 1,140,569 and in Austrian Pat. No. 232,495. These catalysts are especially well suited to use in the cyclo-cooligomerization of this invention since with these catalysts isomerizations of the types which have been observed to a certain extent in the case, for example, of catalysts prepared by means of alkali metals according to German Auslegeschrift No. 1,126,864 do not occur.

The carbonyl-free zerovalent nickel catalysts used in this invention have the additional advantage in the cyclo-co-oligomerization process thereof in that they are catalytically active at lower temperatures than, for example, the catalysts which are prepared according to German Auslegeschrift No. 1,144,268.

The complex compounds of zerovalent nickel described in German Auslegeschrift No. 1,191,375 can also be used as catalysts. In all cases in which substituted conjugated diene starting materials are used, the substituents themselves can be hydrocarbons or functional groups (e.g., alkoxy or carboxylic acid ester groups). They may also be hydrocarbons which contain such functional groups. The only functional groups involved are those which do not enter into any reactions with the catalysts, with the conjugated diene or other reactants or with the unsaturated multicyclic products under the cyclo-co-oligomerization reaction conditions hereof.

The process according to the invention can be performed in the presence of inert solvents, but only those solvents which attack neither the reactants nor the products, nor the catalysts, nor the organometallic components, nor the metal hydrides which were used for the manufacture of the catalyst are suitable. Aliphatic or aromatic hydrocarbons, or aliphatic or cycloaliphatic ethers are used preferentially.

It is particularly advantageous, however, to use the starting conjugated diolefins or the products that can be made according to the process of this invention as solvents in the manufacture of the catalyst, so that a minimum of foreign substances will have to be separated from the reaction product. The process of this invention can be performed at normal pressure of at elevated pressure. The pressure range in that case is determined by the desired direction of the reaction and by the temperature that is needed in each case. The process can be performed at temperatures from $-10°$ to $200°$ C, but preferably at $20°$ to $120°$ C.

Multicyclic, unsaturated, hydrocarbon alicyclic rings can be produced according to the process of this invention in high yields with reference to the non-conjugated diene reactant. The compounds that can be manufactured according to the invention are valuable starting products for further syntheses. They can themselves be further cyclo-co-oligomerized to higher molecular weight compounds which are resinous in nature and are therefore suited to use as molding materials. They can be hydrogenated to saturated compounds and as such used as solvents. They can be oxidatively cleaved at one or more saturated site to form aldehydes, alcohols or acids which are themselves useful in a manner and for applications known to be attributed to such functional groups.

Through the co-oligomerization of cyclic acetylenes with butadiene, 4,5-polymethylene-cyclodecatrienes-(1,4,7) can be produced in yields of more than 95% of the reacted cycloalkine:

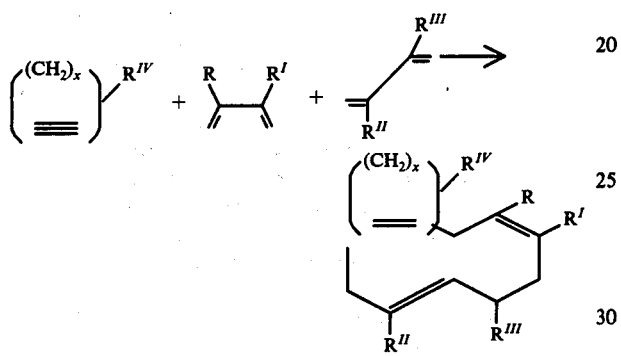

wherein:

R, $R^I$, $R^{II}$, $R^{III}$ and $R^{IV}$ are each hydrogen or a substantially inert substituent such as an alkyl group, e.g., a lower alkyl group of up to about 8 carbon atoms, an aryl group, e.g., a mono or dicyclic phenyl or substituted phenyl moiety having up to about 16 carbon atoms, an alkoxy or aryloxy group or possibly one or more halo groups alone or on an alkyl, alkoxy or aryloxy group.

In an entirely analogous manner, one or more olefinically unsaturated rings (where the olefinic unsaturation is not of the conjugated diene type) cyclo-co-oligomerize with butadiene or a substituted butadiene to form an unsaturated multicyclic product.

In accord with the practice of this invention the conjugated diene reactant or reactants are cyclo-co-oligomerized with one or more cyclic non-benzenoid unsaturated compounds as olefins which are not conjugated dienes or as acetylenes in a reactant mole ratio such that there is preferably one mole of cyclic reactant to two moles of conjugated reactant. While these mole ratios are preferred, it will be clear to one skilled in this art that reactant proportions as low as 10 mole percent of one type of reactant to 90 mole percent of the other type of reactant are suited to use in this invention. Where more than one representative of either type of reactant is used, the individual compounds may be present in mole ratios of about 1 : 10 to 10 : 1 with respect to each other where these are two reactants of a given group. Where these are more than two reactants of a given group, each reactant should represent at least 10 mole percent of its entire group. It is preferred that one conjugated diene react with one cyclic unsaturate in the above-recited mole ratio of about 2 : 1, respectively.

Another aspect of this invention is the cyclo-co-oligomerization of at least one conjugated diene with an alkyl acrylate to form a 10-membered olefinically unsaturated alicyclic ring compound with a carboethoxy pendant group thereon.

It is surprising that the cyclocooligomerization proceeds very smoothly with very high conversions of the acrylic ester to the desired cyclic product with little or no attack on the carboalkoxy group and little or no conversion to open chain compounds. It is believed that this direction of the reaction is due to the particular catalyst being used. These catalysts are per se known materials and are themselves the subject of other patents and patent applications of one or both of the inventors hereof. These catalysts are defined as non-carbonyl-containing zerovalent nickel complex compounds. In particular, zerovalent nickel complexes of nickel with electron donors such as phosphines, phosphites, and multiple olefins are preferred. The reaction of this invention is schematically illustrated below:

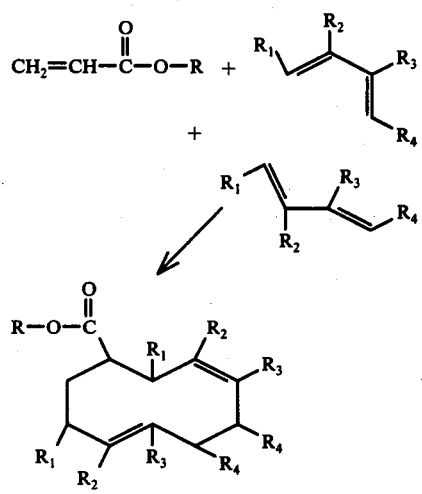

where R is an alkyl group, straight or branched chain, preferably having up to about 8 carbon atoms and wherein $R_1$, $R_2$, $R_3$, and $R_4$ are the same or different and may be hydrogen, alkyl, aryl, alkoxy, aryloxy, halo, haloalkyl, or the like. Alkyl, alkoxy, or haloalkyl groups suitably have up to about 8 carbon atoms in straight or branched chain configuration. Aryl or aryloxy groups suitably have one or two fused or unfused phenyl rings, preferably one, and may have one or several alkyl and-/or halo substituents on one or more of the rings.

Substituted 10 member rings can be produced by the process of the invention in high yields with reference to the acrylate reactant. The compounds that can be manufactured according to the invention are valuable starting products for further synthesis. The unsaturated cyclic products of this invention can be hydrogenated over palladium or Raney nickel catalysts to large ring saturated alcohols which are useful as solvents and as starting materials for dehydrogenation or oxidation to cyclic ketones which are valuable perfume intermediates. The unsaturated cyclic products can be oxidatively cleaved to form di and tri carboxylic acid products which are useful as polyester and polyamide polymerization intermediates.

The following are illustrative of the conjugated dienes which are useful in this invention: butadiene, isoprene, piperylene, chloroprene, ethyl butadiene, ethyl sorbate, phenyl butadiene, etc. The following are illustrative of the acrylates which are useful: methyl acrylate, ethyl acrylate, n-butyl acrylate, 2-ethyl hexyl acrylate, acrylonitrile, etc.

The acrylate monomer and the conjugated diene monomer are suitably admixed in mole ratios of about 1 : 10 to 10 : 1, preferably about 1 : 2. Where different conjugated dienes and different acrylates are cooligomerized, each member of the group should constitute at least about 20% of its group. It is preferred that where several members of each group are used each be employed in substantially equal proportions.

Substituted 12-member rings are obtained, for example, by the simultaneous reaction of butadiene and isoprene in the presence of carbonyl-free catalysts of zero valent nickel. 1-Methyl-cyclododecatriene-(1,5,9) is formed to a major extent, along with a little dimethylcyclododecatriene-(1,5,9), and some cyclododecatriene-(1,5,9).

If butadiene is introduced into a solution of a catalyst - nickel-(O) : tri-(O-phenylphenyl)-phosphite = 1 : 1 - in isoprene; a substituted ring compound [1-methylcyclooctadiene-(1,5)] forms in yields close to 90 percent of the reacted isoprene.

According to the invention, many different substituted 8, 10, and 12-member rings can be produced by cyclocooligomerization, according to the following reaction diagrams:

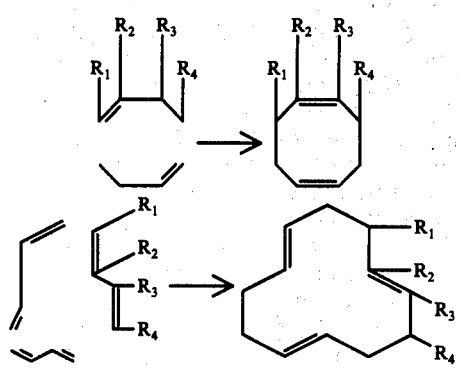

$R_1$, $R_2$, $R_3$, $R_4$ = H or aryl, alkyl or alkoxy radicals; in all of the above formulae at least one R is hydrogen.

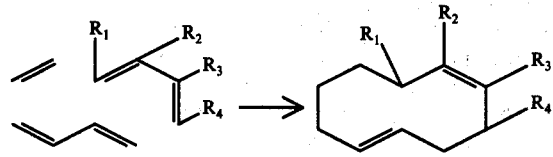

$R_1$, $R_2$, $R_3$, $R_4$ = H or aryl, alkyl or alkoxy radicals; in all of the above formulae at least 1 R is not hydrogen.

According to the invention, another type of cyclocooligomerization of 1,3-diolefins can be achieved, namely, the cyclocooligomerization of 1-disubstituted conjugated dienes with 2- or 2,3-disubstituted conjugated dienes.

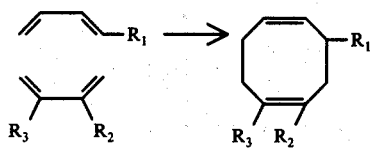

$R_1$, $R_2$, and $R_3$ = aryl or alkyl, or $R_2$ and $R_3$ = H.

Substituted 8, 10, and 12-member rings can be produced by the process of the invention in high yields with reference to the substituted butadiene-(1,3) reactant. The compounds that can be manufactured according to the invention are valuable starting products for further synthesis. For example, 1-substituted and 1,2-disubstituted cyclooctadienes and cyclododecatrienes, as well as 4,5-dimethyl-cyclodecatrienes-(1,4,7) can easily be partially hydrogenated to form the corresponding 1-disubstituted and 1,2-disubstituted cyclomonoolefins, respectively.

In addition to the cyclocooligomerization of two different conjugated dienes, such as butadiene and isoprene, according to this invention, another aspect of this invention resides in the cyclocooligomerization of two different conjugated dienes and an additional unsaturated copolymerizable monomer or monomers which additional monomer or monomers are acetylenically or olefinically unsaturated but are not themselves conjugated dienes. Thus, according to this aspect of this invention, two or more different conjugated dienes, preferably two, are cyclocooligomerized under the same reaction conditions and catalyst as set forth above, with a monoolefinic or acetylenic comonomer to form a substituted alicyclic compound having at least 10 carbon atoms and at least two locations of unsaturation in the ring, and at least one substituent pendent from the ring.

The additional (third) monomer may be one or more of the following types of compounds: acetylene, substituted acetylene, e.g., butine-1, ethylene, styrene, acrylonitrile, acrylic acid esters, and the like. The cyclocooligomerization, in this aspect of this invention the portion of the additional monomer pendent from the unsaturation therein, will form an additional pendent substituent on the alicyclic product. Thus, if butadiene, isoprene and propylene, for example, were cyclocooligomerized according to this invention, an alicyclic product having at least 10 carbon atoms in the ring and at least two methyl groups pendent from the ring would result.

It is within the scope of this invention to utilize acyclic or cyclic unsaturated reactants of the monounsaturated or conjugated diene type.

The substituted 8-, 10-, and 12-membered alicyclic rings, whether or not unsaturated, can be used as solvents.

Further, these unsaturated ring compounds can be oxidatively cleaved to produce long-chain acids, aldehydes and alcohols which have known utility in the plasticizer and detergent arts.

This invention will be illustrated by the following examples in which parts and percentages are by weight unless expressly stated to the contrary.

EXAMPLE 1

4.34 g = 17.05 mmoles of nickel acetyl acetonate and 9.19 g = 17.05 mmoles of tri-(o-phenylphenyl)-phosphite are reduced in 85 cc of benzene in which about 10 g of butadiene are dissolved, with 4,43 g = 34.1 mmoles of monoethoxydiethyl aluminum, at 0° to 20° C. In two hours approximately 250 g of butadiene per hour (total 680 g) are introduced into the catalyst solution at 60° C over a period of about two hours and forty minutes, with the simultaneous drop-by-drop addition of about 60 g of isoprene per hour (total 165 g). The reaction is interrupted, and distillation is performed directly from the reaction vessel at $10^{-4}$ torr and a bath temperature of no more than 100° C. 766 g of product are obtained, having the following compositions:

15.5 g = 2.0% 4-vinylcyclohexene
4.3 g = 0.6% mono-substituted 4-vinylcyclohexene
5.2 g = 0.7% p-diprene
610.0 g = 79.7% cyclooctadiene-(1,5)
119.5 g = 15.6% 1-methylcyclooctadiene-(1,5)
7.4 g = 0.9% dimethylcyclooctadiene-(1,5) 1.1 g = 0.1% cyclododecatriene-(1,5,9) 1.8 g = 0.2% 1-methyl-cyclododecatriene-(1,5,9)
0.7 g = 0.1% dimethylcyclododecatriene-(1,5,9)
0.4 g = 0.1% trimethylcyclododecatriene-(1,5,9)

The yield of 1-methylcyclooctadiene-(1,5) amounts to 82 percent of the theory with reference to reacted isoprene (approximately 50 percent transformation).

The 1-methylcyclooctadiene-(1,5) (B.P.$_{14}$ = 59.5° C, $n_D^{20}$ = 1.49.10), which has not been described hitherto, was characterized by infrared, $H^1$ nuclear magnetic resonance [NMR] and mass spectrometry. At normal pressure and 20° C, it can easily be partially hydrogenated to 1-methylcyclooctene using Raney nickel as the catalyst, with the absorption of 1 mole of $H_2$. Oxidative cleavage produces 8-ketononane-aldehyde.

EXAMPLE 2

The same catalyst was manufactured as described above, but in isoprene instead of benzene. For a period of 28 hours, at a reaction temperature that is slowly increased from 30° C to 52° C, approximately 20 g of butadiene per hour are introduced (total about 600 g butadiene). After distillation as in Example 1, 686 g of a product is obtained having the following composition:

11.2 g = 1.6% 4-vinylcyclohexene
8.2 g = 1.2% mono-substituted 4-vinylcyclohexene
4.5 g = 0.7% p-diprene
517.0 g = 75.3% cyclooctadiene-(1,5)
125.7 g = 18.3% 1-methylcyclooctadiene-(1,5)
3.7 g = 0.5% dimethylcyclooctadiene-(1,5)
1.5 g = 0.2% cyclododecatriene-(1,5,9)
1.5 g = 0.2% 1-methylcyclododecatriene-(1,5,9)
13.0 g = 1.9% higher oligomers The yield of 1-methylcyclooctadiene-(1,5), with reference to reacted isoprene (approximately 21 percent transformation), amounts to about 84 percent of the theory.

EXAMPLE 3

Catalyst (twice the amount) and procedure as in Example 1. Instead of the phosphite, however, the corresponding amount (4.45 g) of triphenylphosphine is used. At a temperature of 60° C approximately 30 g of butadiene per hour (total 250 g) are introduced into the catalyst solution and at the same time 25 g of isoprene [per hour] is added in drop-by-drop fashion. After distillation as in Example 1, 362 g of product are obtained having the following composition:

61.6 g = 17.0% 4-vinylcyclohexene
19.5 g = 5.4% mono-substituted 4-vinylcyclohexene
15.9 g = 4.5% p-diprene
124.8 g = 34.6% cyclooctadiene-(1,5)
74.0 g = 20.5% 1-methylcyclooctadiene-(1,5)
17.5 g = 4.8% dimethylcyclooctadiene-(1,5)
2.1 g = 0.6% ?
7.7 g = 2.2% cyclododecatriene-(1,5,9)
15.4 g = 4.2% 1-methylcyclododecatriene-(1,5,9)
6.2 g = 1.7% dimethylcyclododecatriene-(1,5,9)
5.6 g = 1.6% ?
4.1 g = 1.2% trimethylcyclododecatriene-(1,5,9)
6.9 g = 1.9% higher oligomers The yield of 1-methylcyclooctadiene-(1,5), with reference to the reacted isoprene (37 percent transformation) amounts to 40 percent of the theory.

EXAMPLE 4

The catalyst (1.5 times the amount as in Example 1) is prepared in approximately one liter of piperylene (740 g). For 28 hours, approximately 45 g of butadiene per hour (total 1280 g) are introduced into this solution at a temperature of initially 44° C and after six hours finally at 50° C. After distillation as in Example 1, 1,642 g of product is obtained having the following composition:

22.9 g = 1.4% 4-vinylcyclohexene
5.1 g = 0.3% mono-substituted 4-vinylcyclohexene
3.8 g = 0.2% disubstituted 4-vinylcyclohexene
970.0 g = 59.1% cyclooctadiene-(1,5)
592.0 g = 36.9% 3-methylcyclooctadiene-(1,5)
44.0 g = 2.6% dimethylcyclooctadiene-(1,5)
4.4 g = 0.3% higher oligomers The yield of 3-methylcyclooctadiene-(1,5), with reference to the reacted piperylene (51 percent transformation), amounts to 86.4 percent of the theory.

EXAMPLE 5

Catalyst and procedure as in Example 1.

52 g of 2-phenyl-butadiene are placed in the reaction vessel and 50 g of butadiene per hour are introduced for six hours at 80° C. After distillation, 342.4 g of product are obtained having the following composition:

9.5 g = 2.8% 4-vinylcyclohexene
280.3 g = 81.9% cyclooctadiene-(1,5)
7.2 g = 2.1% mono-substituted 4-vinylcyclohexene
42.2 g = 12.3% 1-phenylcyclooctadiene-(1,5)
3.2 g = 0.9% higher oligomers The yield of 1-phenylcyclooctadiene-(1,5), with reference to the reacted 2-phenyl-butadiene (transformation 64 percent), amounts to 81 percent of the theory.

The 1-phenylcyclooctadiene-(1,5) (B.P.$_{14}$ - 155° C; $n_D^{20}$ 1,5764) can be hydrogenated catalytically in part to phenyl-cyclooctane (B.P.$_{14}$ = 140° C; $n_D^{20}$ 1.5319).

EXAMPLE 6

Catalyst and procedure as in example 1.

60.1 g = 1-methoxy-butadiene are heated to 60° C together with the catalyst solution and for twenty hours approximately 30 g of butadiene per hour (total 620 g) are introduced. 661 g of a product are obtained having the following composition:

16.6 g = 2.5% 4-vinylcyclohexene
571.0 g = 86.3% cyclooctadiene-(1,5)
1.6 g = 0.2% mono-substituted 4-vinylcyclohexene
68.6 g = 10.4% 3-methoxycyclooctadiene-(1,5)
3.0 g = 0.5% higher oligomers The yield of 3-methoxycyclooctadiene-(1,5), with reference to the reacted 1-methoxy-butadiene (transformation 85 percent), amounts to 94 percent of the theory. This 3-methoxycyclooctadiene-(1,5) B.P.$_{20}$: 86° C, $n_D^{20}$ : 1.4887) can easily be hydrogenated catalytically with the absorption of 2 moles of $H_2$ to form the likewise previously undescribed methylcyclooctyl ether (B.P.$_{20}$: 75° to 76° C, $n_D^{20}$: 1,4578). Both compounds were characterized by their infrared, $^1H$ NMR and mass spectra.

EXAMPLE 7

Catalyst (1,5 times the amount) and procedure as in Example 1. The catalyst solution is mixed with 122 g of 5-methyl-heptatriene-(1,3,6). At 60° C, approximately 10 g of butadiene per hour were introduced for 28 hours (total about 290 g). 353 g are obtained of a product having the following composition:

6.0 g = 1.7% 4-vinylcyclohexene
238.0 g = 67.5% cyclooctadiene-(1,5)
3.3 g = 1.2% mono-substituted 4-vinylcyclohexene
105.2 g = 29.8% 3-(butene-(1)-yl-(3)-cyclooctadiene

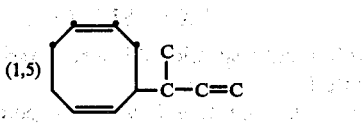

The yield of substituted butadiene, with reference to the reacted 5-methyl-heptatriene (60 percent transformation) amounts to 96.3 percent of the theory The 3-(butene-[1]-yl-[3])-cyclooctadiene-(1,5) is not isolated as such, since when it is greatly heated, it is inclined to enter Cope's transposition as 1,5-diene. The catalytic hydrogenation produces sec-butyl-cyclooctane (B.P.$_{21}$: 111.5° C, $n_D^{20}$: 1.4648) with the absorption of 3 moles of $H_2$.

The hydrocarbon was characterized on the basis of its $H^1$ NMR and mass spectra.

EXAMPLE 8

Catalyst and procedure as in Example 1.

77.2 g of 2,3-dimethyl-butadiene are heated to 60° C together with the catalyst. For 16 hours, approximately 30 grams of butadiene per hour (total 460 g) is introduced, and 494.5 g of product is obtained having the following composition:

11.9 g = 2.4% 4-vinylcyclohexene
425.0 g = 85.9% cyclooctadiene-(1,5)
50.4 g = 10.2%, 1,2-dimethyl-cyclooctadiene-(1,5)
4.2 g = 0.8% disubstituted 4-vinylcyclohexene
3.0 g = 0.6% higher oligomers The yield of 1,2-dimethyl-cyclooctadiene-(1,5), with reference to the reacted 2,3-dimethyl-butadiene (45 percent transformation), amounts to 93 percent of the theory.

The 1,2-dimethyl-cyclooctadiene-(1,5) B.P.$_{18}$ : 78.5° C; $n_D^{20}$: 1.4941), which has not been described hiterto, can easily be hydrogenated, with Raney nickel as the catalyst, partially to 1,2-dimethyl-cyclooctene, from which n-decadione-(2,9) (MP 63° to 64° C) is obtained by oxidative decomposition.

EXAMPLE 9

Catalyst and procedure as in Example 1.

232 g of n-octatriene-(1,3,6) are heated with the catalyst solution to 80° C, with the introduction of butadiene. In 1.5 hours, approximately 400 g of butadiene are absorbed. 527 g of product are obtained having the following composition:

8.7 g = 1.6% 4-vinylcyclohexene
326.9 g = 62.1% cyclooctadiene -(1,5)
11.3 g = 2.1% monosubstituted 4-vinylcyclohexene
178.8 g = 33.9% 3-(butene-[2]-yl-[1])-cyclooctadiene-(1.5)

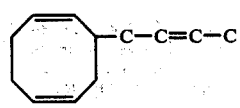

1.5 g = 0.3% higher oligomers.

The yield of 3-substituted cyclooctadiene-(1,5), with reference to the reacted n-octatriene-(1,3,6) (transformation 55 percent), amounts to 93 percent of the theory.

Catalytic hydrogenation produces n-butyl-cyclooctane (B.P.$_{14}$: 107° C, $n_D^{20}$: 1.4609) with the absorption of 3 moles of $H_2$. The hydrocarbon was unequivocally characterized by its infrared and mass spectra.

EXAMPLE 10

The same catalyst as in Example 1 is reduced in a mixture of 340 g of piperylene and 432 g of isoprene with the addition of 17 g of butadiene, and the reaction mixture is heated for 96 hours in an autoclave at 55° to 57° C. After distillation as in Example 1, 713 g of product are obtained having the following composition:

50.7 g = 7.3% 5 unknown substance 14.4 g = 2.1% 3-methylcyclooctadiene-(1,5) 15,0 g = 2.2% p-diprene
24.4 g = 3.5% 1-methylcyclooctadiene-(1,5)
22.5 g = 3.2% 6 unknown substance
70.2 g = 10.1% dimethylcyclooctadiene-(1,5) (from piperylene)
68.2 g = 9.7%)
) 1,4- and 2,4-dimethyl cyclooctadiene-(1,5) 236.0 g = 34.1%)
102.0 g = 14.7% dimethylcyclooctadiene-(1,5) (from isoprene)
86.3 g = 12.5% cyclic and open-chain trimers
3.5 g = 0.5% higher oligomers.

EXAMPLE 11

4.34 g = 17.05 mmoles of nickel acetyl acetonate are reduced in 380 g of piperylene with 4.43 g = 34.1 mmoles of ethoxy aluminum diethyl. The catalyst solution is aspirated into an autoclave, and then 50 g of butadiene and 50 atmospheres of ethylene are forced in. Every two days another 50 g of butadiene are forced in. The reaction mixture is allowed to stand for 16 days at 12° to 15° C. The excess ethylene and butadiene is blown off and then hydrogen is immediately forced in under pressure. After no more $H_2$ absorption is to be observed even at 60° C and 100 atmospheres hydrogen pressure, the autoclave is cooled and the excess gas is blown off, and the entire reaction product is distilled. 449 g of product are obtained, which, according to analysis by gas chromatography, has the following composition:

6.3 g = 1.4% ethylcyclohexene
5.4 g = 1.2% cyclooctane
9.4 g = 2.1% ?
24.3 g = 5.4% n-decane
263.0 g = 58.5% cyclodecane
99.3 g = 22.1% methylcyclodecane
1.8 g = 0.4% dimethylcyclodecane
1.3 g = 0.3% ?
21.6 g = 4.8% cyclododecane
16.6 g = 3.7% higher oligomers The yield of methylcyclodecane (B.P.$_{13}$: 92° C) with reference to reacted piperylene (16 percent) amounts to about 75 percent.

EXAMPLE 12

The catalyst is prepared as in Example 11, but instead of piperylene 300 g of isoprene are used. The solution is aspirated into a 2-liter autoclave and mixed with 500 g of butadiene. The reaction mixture stands for five days at room temperature. After hydrogenation as in Example 11, 251 g of product are obtained, having the following composition:

1.5 g = 0.6% ethylcyclohexane
1.5 g = 0.6% ?
1.5 g = 0.6% cyclooctane
23.4 g = 9.4% n-decane
8.0 g = 3.2% iso-undecane (methyldecane)
2.0 g = 0.8% dimethyl-n-decane
149.5 g = 60.0% cyclodecane
39.7 g = 15.9% methyl-cyclodecane
1.0 g = 0.4% ?
15.7 g = 6.3% cyclododecane
2.0 g = 0.8% methyl-cyclododecane
3.5 g = 1.4% higher oligomers The yield of methyl-cyclododecane, with reference to the reacted isoprene (7 percent), amounts to about 72 percent of the theory.

EXAMPLE 13

The catalyst is prepared as in Example 1 and mixed with 400 g of isoprene. 57 atmospheres of ethylene is forced onto the mixture in an autoclave, and then for twenty hours about 25 g of butadiene per hour are injected. After cooling and blowing off to normal pressure, the reaction mixture is distilled as in Example 1. After hydrogenation under pressure with Raney nickel catalyst, 682 g are obtained of a product having the following composition:

10.2 g = 1.5% ethylcyclohexane
5.5 g = 0.8%
8.2 g = 1.2% n-decane
281.0 g = 41.2% cyclooctane
4.1 g = 0.6% ?
68.2 g = 10.0% methylcyclooctane
231.8 g = 34.0% cyclodecane
64.7 g = 9.5% methylcyclodecane
8.2 g = 1.2% higher oligomers The yield of methylcyclooctane and methylcyclodecane, with reference to the reacted isoprene (about 20 percent reacted), amounts to 91 percent of the theory.

EXAMPLE 14

18 g = 65.5 mmoles of Ni(cyclooctadiene -[1,5])$_2$ are mixed in an autoclave with 1082 g of isoprene and 2000 g of butadiene and are allowed to stand for two months at 60° C. After cooling, the catalyst in the reaction mixture is destroyed with 2N HCl with the admission of air. After distillation, 1383 g are obtained of a product of the following composition:

5.5 g = 0.4% two unknown hydrocarbons
47.6 g = 3.3% 4-vinylcyclohexene
77.6 g = 5.6% p-diprene
35.8 g = 2.6% cyclooctadiene-(1,5)
2.5 g = 0.2% unknown hydrocarbons
27.7 g = 2.0% dipentene
558.9 g = 40.4% trans, trans, trans-cyclododecatriene-(1,5,9)
21.6 g = 1.6% trans, trans, cis-cyclododecatriene-(1,5,9)
21.8 g = 1.6% trans, cis, cis-cyclododecatriene-(1,5,9)
224.7 g = 16.2% 1-methyl-cyclododecatriene-(1,5,9) I
80.4 g = 5.8% 1-methyl-cyclododecatriene-(1,5,9) II
17.2 g = 1.2% dimethyl-cyclododecatriene-(1,5,9) I
7.3 g = 0.5% dimethyl-cyclododecatriene-(1,5,9) II
181.2 g = 13.1% higher oligomers A portion of this product is hydrogenated, and by means of preparative gas chromatography methycyclododecane is isolated ($n_D^{20}$ : 1.4718). The hitherto undescribed 1-methylcyclododecatriene-(1,5,9) I boils at 14.5 torr at 118° C. ($n_D^{20}$ 1.5048). The 1-methyl-cyclododecatriene-(1,5,9) II was characterized only by hydrogenation to methylcyclododecane.

The yield of 1-methyl-cyclododecatriene-(1,5,9), with reference to reacted isoprene (27 percent reaction), amounts to 40 percent of the theory.

EXAMPLE 15

Catalyst and quantities of isoprene and butadiene as in Example 11.

The reaction mixture, however, is pumped through a reactor at 110° C with a time of stay of about 60 minutes, the reactor consisting of a copper capillary with a capacity of two liters which is lying in a heating bath and at the extremity of which there is installed a relief valve adjusted 20–50 atmospheres. Total time 2.5 hours. The composition of the products is similar to Example 14, but 150 g of product is formed per hour per gram of nickel in the catalyst.

The yield of 1-methyl-cyclododecatriene-(1,5,9) amounts to 47 percent of the reacted isoprene (35 percent reacted).

EXAMPLE 16

Catalyst and procedure as in Example 14, but 1.08 kg of piperylene is used instead of isoprene. The reaction product obtained is agitated in air until it is virtually colorless. The nickel hydroxide that precipitates is separated by centrifugation and then distilled. 1514 g are obtained of a product having the following composition:

119.2 g = 7.9% 4-vinylcyclohexene
5.4 g = 0.4% two unknown hydrocarbons
26.6 g = 5.7% cyclooctadiene-(1,5)
1.7 g = 0.1% 3-methyl-cyclooctadiene-(1,5)
73.7 g = 4.8% five unknown hydrocarbons
1057.3 g = 69.8% cyclododecatriene
130.0 g = 8.6% 3-methyl-cyclododecatriene-(1,5,9)
40.0 g = 2.6% higher oligomers The yield of 3-methyl-cyclododecatriene-(1,5,9), with reference to reacted piperylene (29 percent reacted) amounts to 53 percent of the theory.

In the distillation, a 3-methyl-cyclododecatriene-(1,5,9) is obtained (B.F.$_{10}$: 105° C, $n_D^{20}$: 1,4968, 92 percent pure) which still has a tcc-cyclododecatriene-(1,5,9)-content of 8 percent. Catalytic hydrogenation yields methyl-cyclododecane in addition to cyclododecane.

EXAMPLE 17

Catalyst as in Example 1. After the addition of 100 g of 20ethylbutadiene, the mixture is heated to 60° C and for two hours approximately 250 g of butadiene are introduced per hour. After distillation as in Example 1, the following is obtained:

| | |
|---|---|
| 8.8 g | 4-vinylcyclohexene |
| 439.0 g | cyclooctadiene-(1,5) |
| 3.9 g | ethyl-substituted 4-vinylcyclohexene |
| 0.6 g | ? |
| 106.1 g | 1-ethyl-cyclooctadiene-(1,5) |
| 3.6 g | diethyl-cyclooctadiene-(1,5) |
| 0.6 g | cyclododecatriene-(1,5,9) |
| 2.3 g | higher hydrocarbons |
| 564.9 g | product |

The yield of 1-ethyl-cyclooctadiene-(1,5), with reference to reacted ethylbutadiene (approximately 70 percent reacted), amounts to 95 percent of the theory.

1-ethyl-cyclooctadiene-(1,5), which has not been described hitherto, (B.P.$_{16}$: 76° C, $n_D^{20}$: 1,4900), was characterized by infrared, H$^1$NMR and mass spectroscopy.

EXAMPLE 18

Catalyst as in Example 1, but half the amount. At 80° C, butadiene is introduced into the catalyst solution and simultaneously 55 g of sorbic acid ethyl ester is added drop by drop over a period of two hours. As the drop-by-drop addition is made, the catalyst turns deep red and the butadiene absorption becomes slower. In 15 hours approximately 320 g of butadiene are reacted. After the usual distillation, the following is obtained:

7.5 g = 2.2% 4-vinylcyclohexene
293.0 g = 85.9% cyclooctadiene-(1,5)
3.9 g = 1.1% six-ring codimers of butadiene and sorbic acid ethyl ester
32.2 g = 9.4% (8-methyl-cyclooctadienyl-(3)-carboxylic acid ethyl ester
4.7 g = 1.4% higher olefins The yield of [1] amounts to 85 percent of the reacted sorbic acid ethyl ester (amount reacted = 50 percent).

The 8-methyl-cyclooctadien-(1,5)-yl-(3)-carboxylic acid ethyl ester (B.P.$_{15}$: 133° C, $n_D^{20}$: 1.484), which has not been described previously, was characterized by infrared, H$^1$ NMR and mass spectra.

EXAMPLE 19

The catalyst was prepared by reducing 4.34 g = 17.05 mmoles of nickel acetyl acetonate and 9.19 g = 17.05 mmoles of tri-(o-phenyl phenyl)-phosphite in 85 cc of benzene, in which about 10 g of butadiene are dissolved, with 4.43 g = 34.1 mmoles of monoethoxydiethyl aluminum at 0° to 20° C.

This catalyst solution was heated together with 114 g of cyclododecine to 40° C, and then for 20 hours, about 30 g of butadiene per hour were fed in. Thereafter all volatile components of the reaction mixture were distilled out at 10$^{-4}$ torr and up to 40° C. The distillation residue, which contained the catalyst in addition to the higher-boiling hydrocarbon product, was dissolved in 300 ml of pentane. The catalyst was destroyed by treatment with 2 N HCl and excess air. The product of catalyst destruction, tri-(o-phenyl-phenyl) phosphite, is substantially insoluble in pentane and was removed from the pentane solution by suction filtration. The resultant solution was cooled and concentrated to yield:

11.6 g = 1.6% 4-vinylcyclohexene
569.4 g = 78.8% cyclooctadiene-(1,5)
9.9 g = 1.4% unknown C$_{10}$ to C$_{20}$ range compounds
122.1 g = 17.0% bi-cyclo-(10,8,0)-eicosatriene-(cis, cis, trans-$\Delta^{1,10}$,3,7)
9.0 g = 1.2% higher oligomers The yield of the novel bicycloeicosatriene, referred to the reacted cyclododecine (68% reacted), was 94% of theoretical.

The bicycloeicosatriene was characterized by infrared, Raman, and by $^1$H- nuclear magnetic resonance spectra and by chemical reactions. Partial hydrogenation over platinum in glacial acetic acid at atmospheric pressure yielded bicyclo-(10,8,0)-eicosadiene-(cis, cis,$\Delta^{1,10}$,3) having a melting point of 77.5° to 80° C. The partial hydrogenated product was 98.6 pure according to gas chromatography. Hydrogenation of the diene product over Raney nickel at 80° C under hydrogen pressure yielded bicyclo-(10,8,0)-eicosene-(cis-$\Delta^{1,10}$) having a melting point of 63.5° to 64° C. The melting point of the bicycloeicosatriene was 89° to 94° C, depending upon the rapidity of heating, because of the rearrangement thereof to a cisdivinylcyclohexene system. This rearrangement is observed in the case of all cyclodeca-(1,5)-dienes and cyclodeca-(1,4,7) trienes. At higher temperatures the rearrangement is to 3,4-divinyl-bicyclo-(10,4,0)-hexadecene-(cis-$\Delta^{1,6}$) which is partially hydrogenated to 3,4-diethyl-bicyclo-(10,4,0)-hexadecene-(cis-$\Delta^{1,6}$) which has a boiling point of 135° to 139° C at 10$^{-4}$ torr and a refraction index $n_D^{20}$ of 1.5045.

EXAMPLE 20

Approximately 200 g of butadiene are introduced per hour into the catalyst solution prepared according to Example 1, at 80° to 90° C for a period of three hours. At the same time, approximately 70 g of bicyclo-(2,2,1)-heptene-(2) are added drop by drop. After vacuum distillation according to Example 1, 636 g of product are obtained, having the following composition:

13.9 g = 2.2% 4-vinylcyclohexene
448.0 g = 70.4% cyclooctadiene-(1,5)
0.6 g = 0.1% cyclododecatriene-(1,5,9)
6.6 g = 1.2% two unknown hydrocarbons
119.8 g = 26.1% tricyclo-(10,2,1,0$^{2,11}$) pentadecadiene-(cis, trans-4,8)

This tricyclopentadecadiene partially isomerizes at high temperature to form cis-4,5-divinyl-tricyclo-(6,2,1,0$^{2,7}$)-undecane (B.P.$_{20}$: 147° C, $n_D^{20}$: 1.5120). Hydrogenation with the absorption of 2 moles of hydrogen produces the corresponding cis-diethyl compound (B.P.$_{20}$: 153° C, $n_D^{20}$: 1,4934). Upon catalytic hydrogenation over platinum is glacial acetic acid, the tricyclopentadecadiene (M.P.: 19.5° to 20° C) yields tricyclo-(10,2,1,0$^{2,11}$)-pentadecane (B.P.$_{20}$: 167° C, $n_D^{20}$: 1.5110).

All of the hitherto undescribed compounds were characterized by their infrared and H$^1$ NMR spectra.

The yield of tricyclo-pentadecadiene, with reference to reacted bicyclo-(2,2,1)-heptene-(2) (39 percent reaction), was 95 percent of the theory.

EXAMPLE 21

The catalyst was prepared as in Example 1. 36 g = 191 mm of cyclotetradecadiine(1,8) were added to the catalyst solution and approximately 50 g of butadiene per hour were introduced at 40° C over about 25 hours. All of the volatiles (benzene, 4-vinylcyclohexene, cyclooctadiene-(1,5)) were removed by vacuum distillation at 0.1 torr and 20° C. Approximately 500 ml of benzene were added to the distillation residue. The tricyclo(20,8,0$^{1,10}$0$^{16,25}$)-triacontahexane-($\Delta^{1,10}$3,7,$\Delta^{16,25}$,18,22) (I) that was formed is practically insoluble in benzene and therefore can be removed by filtration. The catalyst was destroyed by shaking the benzene solution with 2N aqueous HCl solution and with excess air. After drying with calcined Na$_2$SO$_4$, the benzene was distilled off at reduced pressure. The residue was taken up in a little pentane, whereupon the tri-(o-phenylphenyl)-phosphate, being insoluble, is left behind. After the pentane is removed by distillation, bicyclo-(12,8,0)-eicosatriene($\Delta^{1,10}$,3,7)-ine-(16) (II) and unreacted cyclotetradecadiine are separated by fractional crystallization from an ether alcohol mixture. The following product distribution was obtained:

35.5 g = 2.7% 4-vinylcyclohexene
1218.0 g = 94.2% cyclooctadiene-(1,5)
14.8 g = 1.2% (II)

15.2 g = 1.2% (I)
10.0 g = 0.8% higher oligomers and residue.

Substances (I) and (II) were formed in a yield of 93 percent with reference to the cyclotetradecadiine that reacted (conversion = 45 percent).

Substance (I) has a melting point of 160°–164° C, and Substance (II) has a melting point of 98°–101° C. Substances (I) and (II) have been characterized by $H^1$ NMR and infrared spectra. The partial hydrogenation of Substance (I) yields Tricyclo-(20,8,0,0$^{16,25}$)-triacontadiene-($\Delta^{1,10}$,$\Delta^{16,25}$), and the partial hydrogenation of Substance (II) yields bicyclo-(12,8,0)-docosene-($\Delta^{1,10}$).

EXAMPLE 22

The catalyst was prepared by reducing 4.34 g = 17.05 mmoles of nickel acetyl acetonate and 9.19 g = 17.05 mmoles of tri-(o-phenylphenyl)-phosphite in 85 cc of benzene, in which about 10 g of butadiene are dissolved, with 4.43 = 34.1 mmoles of monoethoxy diethyl aluminum at 0° to 20° C. After the addition of 34 g of acrylic acid ethyl ester, approximately 25 g of butadiene were introduced at 60° C for 20 hours. After the customary distillation, the following is obtained after hydrogenation:

6.3 g = 2.1% ethylcyclohexene
233.8 g = 79.0% cyclooctane
17.8 g = 6.0% cyclodecanecarboxylic acid ethyl ester
2.7 g = 0.9% undecanic acid ethyl ester
35.3 g = 11.9% residue.

EXAMPLE 23

A solution of 4.64 g = 17.05 mm of Ni(cyclooctadiene-(1,5))$_2$ and 9.18 g = 1705 mm of tri-(o-phenylphenyl)-phosphite in benzene containing butadiene is used as the catalyst. For 10 hours, at 80° C, approximately 100 g of butadiene are added per hour, and at the same time, a total of about 50 g of acrylic acid ethyl ester are added drop by drop. After the customary distillation and hydrogenation, the following is obtained:

16.1 g = 1.9% ethylcyclohexane
740.0 g = 86.6% cyclooctane
77.1 g = 9.0% cyclodecanecarboxylic acid ester
4.1 g = 0.5% (cis-3,4-diethyl-cyclohexenyl)-carboxylic acid ethyl ester
9.3 g = 1.1% undecanic acid ethyl ester
8.2 g = 1.0% residue and higher oligomers

What is claimed is:
1. 3-Methoxycycloctodiene-(1,5) having a boiling point of 86° C and $n_D^{20}$ of 1.4887.

* * * * *

UNITED STATES PATENT AND TRADEMARK OFFICE
CERTIFICATE OF CORRECTION

PATENT NO. : 4,076,757
DATED : February 28, 1978
INVENTOR(S) : Günther Wilke et al It is certified that error appears in the above-identified patent and that said Letters Patent are hereby corrected as shown below:

Column 5, line 44, insert -- not -- before "hydrogen".

Column 8, line 41, "140°C" should read -- 149°C --.

Column 14, line 34, "is glacial" should read -- in glacial --.

Column 10, lines 22, 23 and 24 should read as follows:
-- 68.2 g = 9.7%)
              ) 1,4- and 2,4-dimethyl cyclooctadiene-(1,5) --.
236.0 g =34.1%)

Signed and Sealed this

Twenty-seventh Day of June 1978

[SEAL]

Attest:

RUTH C. MASON
Attesting Officer

DONALD W. BANNER
Commissioner of Patents and Trademarks